US008999909B2

(12) United States Patent
Merkel et al.

(10) Patent No.: US 8,999,909 B2
(45) Date of Patent: Apr. 7, 2015

(54) AZEOTROPIC COMPOSITIONS OF 1,1,1,3,3-PENTACHLOROPROPANE AND HYDROGEN FLUORIDE

(75) Inventors: Daniel C. Merkel, West Seneca, NY (US); Hsueh Sung Tung, Getzville, NY (US); Konstantin A. Pokrovski, Orchard Park, NY (US); Hang T. Pham, Amherst, NY (US); Ryan Hulse, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 254 days.

(21) Appl. No.: 13/402,983

(22) Filed: Feb. 23, 2012

(65) Prior Publication Data
US 2013/0221272 A1 Aug. 29, 2013

(51) Int. Cl.
*C11D 7/00* (2006.01)
*C07C 19/01* (2006.01)

(52) U.S. Cl.
CPC ....................................... *C07C 19/01* (2013.01)

(58) Field of Classification Search
CPC .............................. C11D 7/5036; C11D 7/505
See application file for complete search history.

(56) References Cited

U.S. PATENT DOCUMENTS

| | | | |
|---|---|---|---|
| 5,710,352 A * | 1/1998 | Tung | 570/166 |
| 6,023,004 A | 2/2000 | Thenappan et al. | |
| 6,328,907 B1 | 12/2001 | Nakada et al. | |
| 6,660,893 B2 | 12/2003 | Ewing et al. | |
| 7,265,082 B2 | 9/2007 | Pham et al. | |
| 7,371,363 B2 | 5/2008 | Merkel et al. | |
| 8,075,797 B2 | 12/2011 | Hulse et al. | |
| 2005/0080302 A1 | 4/2005 | Baker et al. | |
| 2008/0033219 A1 | 2/2008 | Lambert et al. | |
| 2010/0048961 A1 | 2/2010 | Merkel et al. | |
| 2010/0113323 A1 | 5/2010 | Tung et al. | |
| 2011/0201853 A1 * | 8/2011 | Tung et al. | 570/168 |

OTHER PUBLICATIONS

PCT ISR & Written Opinion issued in PCT/US2013/025892 dated May 10, 2013.
Kim et al. ; (Mar. 1996) "A Study to Determine the Existence of an Azeotropic R-22 "Drop-In" Substitute" ; Source: Report from the Building Environment Division of the Building & Fire Research Laboratory of the U.S. Department of Commerce.
G. Morrison & M.O. McLinden ; (1993) "Azeotropy in refrigerant mixtures" ; Source: International Journal of Refrigeration, vol. 16, No. 2, pp. 129-138.

* cited by examiner

*Primary Examiner* — Necholus Ogden, Jr.
(74) *Attorney, Agent, or Firm* — Bruce O. Bradford

(57) ABSTRACT

Provided are azeotropic or azeotrope-like mixtures of 1,1,1,3,3-pentachloro-propane (240fa) and hydrogen fluoride. Such compositions are useful as an intermediate in the production of HFC-245fa and HCFO-1233zd.

1 Claim, 1 Drawing Sheet

P-T-X of 240fa/HF

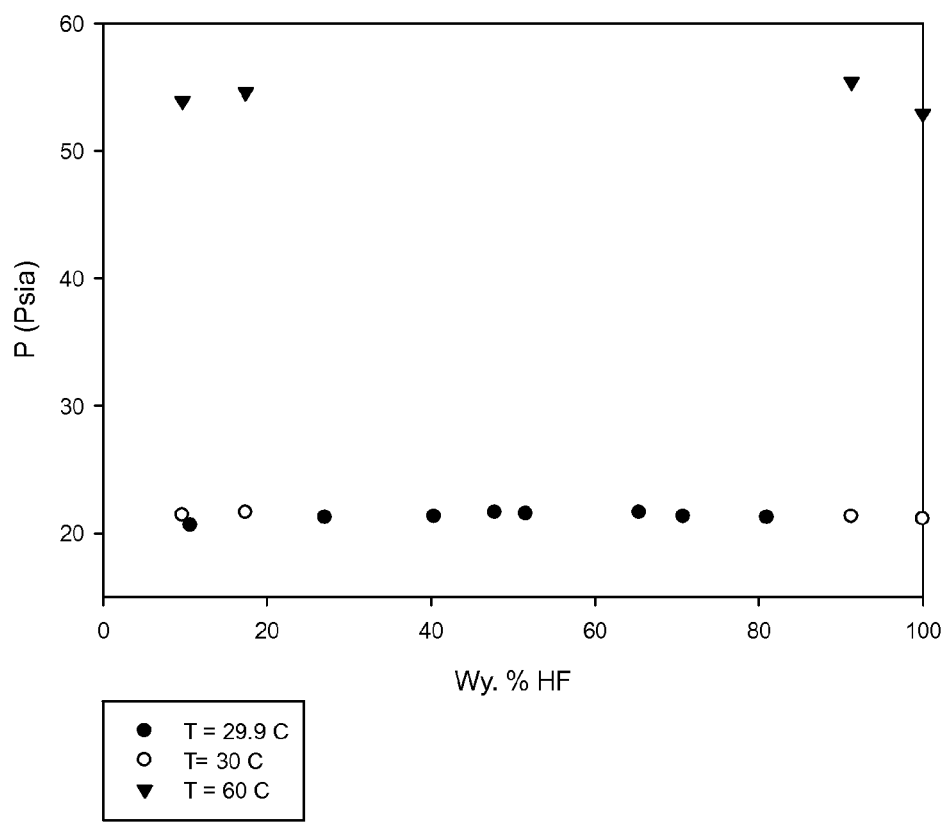

US 8,999,909 B2

AZEOTROPIC COMPOSITIONS OF 1,1,1,3,3-PENTACHLOROPROPANE AND HYDROGEN FLUORIDE

FIELD OF THE INVENTION

The present invention pertains to azeotropic or azeotrope-like compositions of 1,1,1,3,3-pentachloropropane (HCC-240fa or 240fa) and hydrogen fluoride (HF).

BACKGROUND OF THE INVENTION

Chlorofluorocarbon (CFC) based chemicals have been widely use in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is consider to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. 1233zd has a Z-isomer and an E-isomer. Due to differences in the physical properties between these two isomers, pure 1233zd (E), pure 1233zd (Z), or certain mixtures of the two isomers may be suitable for particular applications as refrigerants, propellants, blowing agents, solvents, or for other uses.

The compound 1,1,1,2,3-pentachloropropane (240fa) is a reactant useful in the production of both 245fa and 1233zd. Processes for making these compounds are well known in the art. See for example, U.S. Pat. Nos. 5,763,706 and 6,844,475. See also, U.S. Patent Publication No. 2011-0201853, which provides an integrated process and methods of producing 1233zd (E).

It has now been found that an important intermediate in the production of both 245fa and 1233zd, is an azeotrope or azeotrope-like mixture of 1,1,1,3,3-pentachloro-propane (240fa) and hydrogen fluoride (HF). This intermediate, once formed, may thereafter be separated into its component parts, for example, by extraction or distillation techniques. HCC-240fa has a boiling point of about 178.5° C. and HF has a boiling point of about 20° C. at standard atmospheric pressure. These azeotropic or azeotrope-like compositions find use not only as reactor feeds in the production of 245fa and 1233zd, but they are additionally useful as solvent compositions useful for removing surface oxidation from metals.

SUMMARY OF THE INVENTION

The present invention is directed to azeotropic or azeotrope-like mixtures of 1,1,1,3,3-pentachloropropane (240fa) and hydrogen fluoride. Such compositions are useful as an intermediate in the production of HFC-245fa and HCFO-1233zd.

In certain embodiments of this mixture, the composition comprises effective amounts of 1,1,1,3,3-pentachloro-propane (240fa) and hydrogen fluoride (HF).

In certain embodiments of this mixture, the azeotropic or azeotrope-like composition of the invention consists essentially of from about 90 to about 97 weight percent hydrogen fluoride and from about 10 to about 3 weight percent 1,1,1,3,3-penta-chloropropane (240fa), which composition has a boiling point of about 24° C. to about 60° C. at pressure of about 17.8 psia to pressure of about 55.4 psia.

In certain embodiments of this mixture, the composition consists of hydrogen fluoride and 1,1,1,3,3-pentachloropropane (240fa).

In certain embodiments of this mixture, the composition comprises from about 99 to about 1 weight percent HF.

In certain embodiments of this mixture, the composition comprises from about 40 weight percent to about 97 weight percent HF.

In certain embodiments of this mixture, the composition comprises from about 60 to about 3 weight percent 240fa.

In certain embodiments of this mixture, the composition comprises from about 90 weight percent to about 95 weight percent 240fa.

In certain embodiments of this mixture, the composition comprises from about 10 weight percent to about 5 weight percent 240fa.

In certain embodiments of this mixture, the composition has a boiling point of about from 24° C. to about 60° C. at a pressure from about 17.8 psia to about 55.4 psia.

In certain embodiments of this mixture, the invention is directed to an azeotropic or azeotrope-like composition having about 92±2 weight percent HF and about 8±2 weight percent 240fa has a boiling point of about 24° C. at 17.8 psia.

Another aspect of the present invention is directed to a method of forming an azeotropic or azeotrope-like composition which comprises blending hydrogen fluoride and 1,1,1,3,3-pentachloropropane (240fa), which composition has a boiling point of about 24° C. to about 60° C. at pressure of about 17.8 psia to pressure of about 55.4 psia.

In certain embodiments of this method, the composition consists essentially of from about 90 to about 97 weight percent hydrogen fluoride and from about 10 to about 3 weight percent 1,1,1,3,3-pentachloropropane (240fa).

In certain embodiments of this method, the composition consists of hydrogen fluoride and 1,1,1,3,3-pentachloropropane (240fa).

In certain embodiments of this method, the composition consists essentially of about 92±2 weight percent HF and about 8±2 weight percent 240fa and has a boiling point of about 24° C. at 17.8 psia.

Another aspect of the present invention is directed to a method of forming a heterogeneous azeotropic or azeotrope-like composition which comprises blending from about 0.2 to about 97 weight percent hydrogen fluoride and from about 99.8 to about 3 weight percent 1,1,1,3,3-pentachloropropane (240fa), which composition has a boiling point of about from 24° C. to about 60° C. at pressure of about from 17.8 psia to about 55.4 psia.

In certain embodiments of this method, the composition comprises from about 99 to about 1 weight percent HF.

In certain embodiments of this method, the composition comprises from about 40 weight percent to about 97 weight percent HF.

In certain embodiments of this method, the composition comprises from about from about 90 to about 97 weight percent HF.

In certain embodiments of this method, the composition comprises from about 60 to about 3 weight percent 240fa.

In certain embodiments of this method, the composition comprises from about 90 weight percent to about 95 weight percent 240fa.

In certain embodiments of this method, the composition comprises from about 10 weight percent to about 3 weight percent 240fa.

In certain embodiments of this method, the composition has a boiling point of about from 24° C. to about 60° C. at a pressure from about 17.8 psia to about 55.4 psia.

Another aspect of the present invention is directed to a method of separating 240fa from the azeotropic like mixture of 240fa and HF comprising the step of extracting the HF from the mixture.

In certain embodiments of this method, the extraction of HF is accomplished using water or other aqueous solution.

In certain embodiments of this method, the extraction of HF is accomplished using sulfuric acid.

In certain embodiments of this method, the extraction of HF is accomplished by distillation.

In certain embodiments of this method, the distillation comprises extractive distillation.

In certain embodiments of this method, the distillation comprises pressure swing distillation.

BRIEF DESCRIPTION OF THE DRAWINGS

FIG. 1 shows a plot of the vapor pressures of the mixtures formed in Example 1 and Example 2 as measured at 30° C. and 60° C.

DETAILED DESCRIPTION OF THE INVENTION

The present invention provides a heterogeneous azeotropic composition consisting essentially of 1,1,1,3-pentachloropropane (240fa) and hydrogen fluoride (HF).

The invention further provides an azeotropic or azeotrope-like composition which consists essentially of from about 90 to about 97 weight percent hydrogen fluoride and from about 10 to about 3 weight percent 1,1,1,3,3-pentachloropropane (240fa), which composition has a boiling point of about 24° C. to about 60° C. at pressure of about 17.8 psia to pressure of about 55.4 psia.

The invention also provides a method of forming a heterogeneous azeotropic or azeotrope-like composition which consists essentially of blending from about 0.2 to about 97 weight percent hydrogen fluoride and from about 99.8 to about 3 weight percent 1,1,1,3,3-pentachloropropane (240fa), which composition has a boiling point of about— from 24° C. to about 60° C. at pressure of about from 17.8 psia to about 55.4 psia.

When 1,1,1,3,3-pentachloropropane (240fa) and HF were added to a vessel, it was observed that 240fa forms an azeotropic or azeotrope-like mixture with HF. The unreacted 240fa/HF intermediate was found in the vapor space of the vessel.

The thermodynamic state of a fluid is defined by its pressure, temperature, liquid composition and vapor composition. For a true azeotropic composition, the liquid composition and vapor phase are essentially equal at a given temperature and pressure. In practical terms this means that the components cannot be separated during a phase change.

For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling.

For the purpose of this invention, azeotropic compositions are defined to include azeotrope-like compositions, which means, a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of hydrogen fluoride and 240fa to form an azeotropic or azeotrope-like composition. By effective amount is meant an amount of each component which, when combined with the other component, results in the formation of an azeotrope or azeotrope-like mixture. The inventive compositions preferably are binary azeotropes which consist essentially of combinations of only hydrogen fluoride with 240fa.

In the preferred embodiment, the inventive composition contains from about 99 to about 1 weight percent HF, preferably from about 1 weight percent to about 99 weight percent and most preferably from about 40 weight percent to about 97 weight percent. In the preferred embodiment, the inventive composition contains from about 60 to about 3 weight percent 240fa preferably from about 90 weight percent to about 95 weight percent and most preferably from about 10 weight percent to about 5 weight percent. The composition of the present invention has a boiling point of about from 24° C. to about 60° C. at a pressure from about 17.8 psia to about 55.4 psia. An azeotropic or azeotrope-like composition having about 92±2 weight percent HF and about 8±2 weight percent 240fa has been found to boil at about 24° C. and 17.8 psia.

The following non-limiting examples serve to illustrate the invention.

EXAMPLE 1

9 g of 1,1,1,3,3-pentachloropropane (240fa) were dissolved in 14.7 g of HF to form a heterogeneous azeotrope mixture. This experiment was done at 24° C., and at 17.8 psia.

EXAMPLE 2

Binary compositions containing solely 1,1,1,3,3-pentachloropropane (240fa) and HF are blended to form a heterogeneous azeotrope mixtures at different compositions. The vapor pressures of the mixtures are measured at about 29.9° C., 30° C. and 60° C. and the following results are noticed.

Tables 1 and 2 show the vapor pressure measurement of 240fa and HF as a function of composition of weight percent HF at constant temperatures of about 29.9° C., 30° C. and 60° C.

TABLE 1

P-T-X of 240fa/HF at T = 30° C. and 60°

P (Psia)

| Wt. % HF | T = 30° C. | T = 60° C. |
|---|---|---|
| 0 | 0.4 | 0.69 |
| 9.7 | 21.4 | 53.9 |
| 17.4 | 21.6 | 54.6 |
| 91.3 | 21.3 | 55.4 |
| 100 | 21.1 | 52.9 |

As shown in Table 1, variation of the amount of HF in the composition shows no significant (+/−0.3 psia or less) change in pressure at 30° C., and similarly no significant change in pressure (+/−0.8 psia) at 60° C., supporting the azeotrope-like nature of the composition over this range of HF in the composition.

TABLE 2

P-T-X of 240fa/HF at T = 29.9°

| Wt. % HF | P (psia) |
|---|---|
| 0 | 0.4 |
| 10.7 | 20.6 |
| 27.1 | 21.2 |
| 40.4 | 21.3 |
| 47.8 | 21.6 |
| 51.6 | 21.5 |
| 65.4 | 21.6 |
| 70.8 | 21.3 |
| 81.0 | 21.2 |
| 100 | 21.1 |

As shown in Table 2, variation of the amount of HF in the composition shows no significant (+/−1 psia or less) change in pressure at 29.9° C., supporting the azeotrope-like nature of the composition over this range of HF in the composition.

These data show that the mixture is an azeotrope or azeotrope-like since the vapor pressures of mixtures of 240fa and HF are higher, at all indicated blend proportions, than 240fa and HF alone, i.e., as indicated in the first and last rows when HF is 0.0 wt % and 240fa is at 100.0 wt % as well as when 240fa is at 0.0 wt % and HF is at 100.0 wt. %. The data from Table 1 are shown in graphic form in FIG. 1.

EXAMPLE 3

The azeotropic composition of the 240fa/HF mixture is also verified by Vapor-Liquid-Liquid Equilibrium (VLLE) experiment.

62.6 g of 1,1,1,3,3-pentachloropropane (240fa) are dissolved in 31.6 g of HF to form a heterogeneous mixture (visual observation) at 24° C. The vapor compositions of the mixture were sampled at room temperature of 24° C. The result shows that the azeotropic composition is about 92±2 wt % HF at 24° C.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An azeotropic or azeotrope-like liquid composition which consists of from about 90 to about 97 weight percent hydrogen fluoride and from about 10 to about 3 weight percent 1,1,1,3,3-pentachloropropane (240fa), which composition has a boiling point of about 24° C. to about 60° C. at pressure of about 17.8 psia to pressure of about 55.4 psia.

* * * * *